United States Patent
Aral et al.

(10) Patent No.: US 6,838,186 B2
(45) Date of Patent: Jan. 4, 2005

(54) MULTILAYER ORIENTED ANTIMICROBIAL AND ANTIFOGGING FILMS

(75) Inventors: Oktay Aral, Manisa (TR); Zakir Rzaev, Manisa (TR); Cumhur Buyukakinci, Manisa (TR)

(73) Assignee: Polinas Plastic of America, Inc., Fort Lee, NJ (US)

( * ) Notice: Subject to any disclaimer, the term of this patent is extended or adjusted under 35 U.S.C. 154(b) by 226 days.

(21) Appl. No.: 10/128,630

(22) Filed: Apr. 22, 2002

(65) Prior Publication Data

US 2003/0203229 A1 Oct. 30, 2003

(51) Int. Cl.⁷ .......................... B32B 27/32; A01N 25/34
(52) U.S. Cl. .................. 428/516; 424/402; 424/404; 428/332; 428/336; 428/347; 428/910
(58) Field of Search .................. 424/402, 404; 428/213, 214, 215, 216, 332, 335, 336, 347, 516, 910

(56) References Cited

U.S. PATENT DOCUMENTS

| | | | |
|---|---|---|---|
| 3,888,978 A | 6/1975 | Düwel et al. | 424/199 |
| 3,907,720 A | 9/1975 | Field et al. | 424/78 |
| 3,991,187 A | 11/1976 | Högberg et al. | 424/199 |
| 4,000,102 A | 12/1976 | Shima et al. | 260/234 |
| 4,008,351 A | 2/1977 | Inoue et al. | 428/411.1 |
| 4,066,811 A | 1/1978 | Naito et al. | 428/220 |
| 4,072,790 A | 2/1978 | Creekmore et al. | 428/220 |
| 4,261,914 A | 4/1981 | Shakhtakhtinsky et al. | |
| 4,314,851 A | 2/1982 | ogly Shakhtakhtinsky et al. | 106/16 |
| 4,341,825 A | 7/1982 | Kemski | 428/347 |
| 4,486,552 A | 12/1984 | Niemann | 523/169 |
| 4,584,192 A | 4/1986 | Dell et al. | 424/81 |
| 4,661,477 A | 4/1987 | Görög nee Privitzer et al. | 424/199 |
| 4,751,141 A | 6/1988 | Fink et al. | 428/326 |
| 4,876,146 A | 10/1989 | Isaka et al. | 428/347 |
| 4,935,232 A | 6/1990 | McIntosh | 424/78 |
| 4,938,955 A | 7/1990 | Niira et al. | 424/79 |
| 4,956,209 A | 9/1990 | Isaka et al. | 428/35.2 |
| 5,104,306 A | 4/1992 | Gordon et al. | 425/503 |
| 5,108,740 A | 4/1992 | Greenwald et al. | 424/78.32 |
| 5,142,010 A | 8/1992 | Olstein | 526/248 |
| 5,152,946 A | 10/1992 | Gillette | 264/230 |
| 5,178,495 A | 1/1993 | Cameron | 405/303 |
| 5,246,659 A | 9/1993 | Crighton et al. | 264/290.2 |
| 5,527,570 A | 6/1996 | Addeo et al. | 428/35.7 |
| 5,567,372 A | 10/1996 | Nohr et al. | 264/103 |
| 5,569,732 A | 10/1996 | Nohr et al. | 528/27 |
| 5,614,568 A | 3/1997 | Mawatari et al. | 523/122 |
| 5,777,010 A | 7/1998 | Nohr et al. | 524/188 |
| 5,962,092 A | * 10/1999 | Kuo et al. | 428/34.9 |

FOREIGN PATENT DOCUMENTS

| | | |
|---|---|---|
| EP | 0784067 | 7/1997 |
| GB | 1270922 | 4/1972 |
| GB | 2225580 A | 6/1990 |
| JP | 4013733 | 1/1992 |
| JP | 4202313 | 7/1992 |
| JP | 4270742 | 9/1992 |
| JP | 4275142 | 9/1992 |
| JP | 4363346 | 12/1992 |
| JP | 7082440 | 3/1995 |
| JP | 9002517 | 1/1997 |
| JP | 9076339 | 3/1997 |
| JP | 9077042 | 3/1997 |
| JP | 9077880 | 3/1997 |
| JP | 9077938 | 3/1997 |
| JP | 9085847 | 3/1997 |
| JP | 9095545 | 4/1997 |
| JP | 9104092 | 4/1997 |
| JP | 9108084 | 4/1997 |
| JP | 9123264 | 5/1997 |
| JP | 9135716 | 5/1997 |
| JP | 9136973 | 5/1997 |
| JP | 9136980 | 5/1997 |
| JP | 9151317 | 6/1997 |
| JP | 9169073 | 6/1997 |
| JP | 9165447 | 7/1997 |
| JP | 9176370 | 7/1997 |
| JP | 6317372 | 7/1998 |
| JP | 11157022 | * 6/1999 |
| JP | 2000119412 | * 4/2000 |

* cited by examiner

*Primary Examiner*—D. S. Nakarani
(74) *Attorney, Agent, or Firm*—Ellis & Venable PC

(57) ABSTRACT

Antimicrobial and antifogging polymeric films with preferable A/C/E structure useful for the food, medicine and agriculture applications as well as for other general packaging and non-traditional special applications. More preferably, antimicrobial and antifogging films having a A/B/C/E structure. Most preferably, antimicrobial and antifogging films having a A/B/C/D/E structure. A multilayer structure (having at least an skin layer (A) having antifogging and antimicrobial properties/a core layer (C)/an outer layer (E) structure) for semi and biaxially oriented polyolefin based antifogging films having advantageous properties as compared with known and commercial films such as low values of haze, high values of sheen, lower longitudinal and transverse shrinkage, which provides high dimensional stability, and excellent antifogging and antimicrobial properties. Preferably the skin layer (A), having antifogging and antimicrobial properties, is electrical corona or flame treated. Electrical corona or flame treatment of the outer layer (E) may enhance ink anchorage and increase the printability of this layer. Preferably, the films comprise an inner (B) layer between the skin layer (A) and the core layer (C). Preferably, the films may comprise a second inner (D) layer between the outer (E) layer and the core layer (C).

50 Claims, No Drawings

MULTILAYER ORIENTED ANTIMICROBIAL AND ANTIFOGGING FILMS

FIELD OF THE INVENTION

The present invention relates to the field of plastic fabrication and uses. More specifically, the present invention relates to multilayered plastic films that have antifogging and antimicrobial properties.

BACKGROUND

It is known that many thermoplastic polymer packaging materials, such as films, coatings, sheets, bags, and the like, with suitable strength and flexibility are used to enclose perishable foods, fruits, raw meats, daily dishes and vegetables. These packaging materials tend to discolor and fog during extended storage. Because of this, polymer packaging materials have to possess the following characteristics: (1) suitable thickness and cohesive properties for packaging, (2) high antifogging properties, i.e. the films do not accumulate water droplets on the surface of the material, (3) high mechanical strength at break, (4) appropriate slip properties, (5) excellent optical characteristics, such as gloss and transparency, and (6) sealability under heat.

There is a high demand in the packaging food industry, agriculture, industrial markets, flower wrapping trade, and the like for biaxially oriented thin antifogging films of different types that can be used for both food-wrapping and agricultural applications. The antifogging and antimicrobial films reduce the growth of living contaminants (such as bacteria and molds) and ensure that any condensation of water vapor occurs as an uniform, invisible, layer of water rather than as a series of individual droplets which are not only aesthetically undesirable but produce damaging effects.

The several goals of these films are: (1) to ensure that the polymer thin films retain their transparency so that the packaged contents are clearly visible and so that there is maximum light transmission into the enclosure, (2) to protect the packaged food products from undesired degradation that may be caused by the droplets of water, (3) to prevent large drops of condensed water from falling onto young plants, increasing the possibility of damage and disease, (4) to prevent plant "burning" caused by large drops of water lensing (concentrating and focusing) solar radiation onto the contents of the package, (5) to provide antimicrobial properties and (6) to provide prolonged shelf life by preventing the growth of the certain bacteria.

Currently, antifogging films (also known as antifog or antimist films) are produced by adding or coating various types of organic antifogging additives, such as ethoxylated sorbitan ester, glyceride fatty acid ester, glycerol stearate (or monostearate), glycerol oleate and sorbitan ester, and the like, to conventional film forming polymers, such as polyolefins, flexible vinyl chloride polymers, oriented styrene polymers, polyesters, ethylene-vinyl acetate copolymers, and the like.

There are a number of available patent publications related to antifogging polymer films obtained by using different types of thermoplastic film-forming/antifogging additives as discussed below. These patents relate to systems such as a biaxially stretched film with a base of an olefin polymer resin composition containing ethylene-propylene copolymer and 0.5% of polyethylene glycol stearyl ether, olefin polymer/fatty acid monoester of polyhydric alcohol (or alkaline metal salt of a diester of sulfosuccinic acid), polyolefin/ethylene oxide (or monoglyceride of a fatty acid), polystyrene/alkyl phenyl polyethylene glycol ether (of fatty alcohol sulfate) base coating, polyethylene/polyhydric alcohol esters or metal salts of either saturated or unsaturated monocarboxylic fatty acids, ethylene polymer and polybutene blend/glyceride with acyl group, and ethylene-acrylic acid (or ethyl acrylate and/or vinyl acetate) copolymers or low density ethylene polymers/alkyl phenyl polyethylene glycol ethers or alkoxylated alkyl phenol. But all of these patents suffer from one or more of the following disadvantages such as higher haze values, low values of sheen, higher transverse or longitudinal shrinkage, and poor antifogging properties.

More specifically, in U.S. Pat. No. 4,066,811, there is disclosed raw tubular polyolefin films with suitable orientation determined by heat shrinkage, containing ethylene-vinyl acetate copolymer, polyethylene, polypropylene or mixtures thereof, polyalkylene ether polyol and non-ionic surfactant-polyhydric alcohol ester derivatives of fatty acids. In the above patent, the determination of antifogging properties of the subject film was according to the following measurements: (1) no water droplets were present on the surface and water was in a uniform layer, (2) large water droplets locally were adhered or there was unevenness in the state of any adhering water droplets, and (3) fine water droplets adhered to the whole surface.

Other recently published patented inventions, such as JP Pat. 09-104,092, relate to various polymer compositions, sheets, and films having fog resistant properties. Disclosed therein are antifogging sheets comprising weather-resistant polycarbonate based films, hot-melt poly (methylmethacrylate) films containing a benzotriazol UV-absorber, and cellulose films containing a diethyl phthalate plasticizer, to form a flat or wavy laminated panel allegedly providing good weather and moisture resistant adhesion.

Antifogging polypropylene lids with smooth handling properties, such as disclosed in JP Pat. 09-76,339, were prepared by thermal formation of polypropylene sheets, where the interior faces of the lids exhibit antifogging property and the exterior faces have a friction coefficient of 0.01–0.7. The plastic of these lids was stretched in the machine direction, coated on the exterior face with poly (dimethylsiloxane) and on the interior face with sugar fatty ester emulsion, and thermal formed into a lid showing no noise when removed from their stack.

Plastic sheets having anisotropic surface characteristics, including fogging and adhesion properties, are disclosed in JP Pat. 09-85,847 and comprise alternating strips of nylon 6–12 and ethylene-methacrylic acid copolymer.

There are antifogging laminated films for agricultural uses that use a polyolefin resin middle layer. This layer frequently consists of high density polyethylene and synthetic rubber with external layers consisting of antifogging agents. One laminate, disclosed in JP Pat. 0994,930, comprises an ethylene-vinyl acetate copolymer middle layer, uses KFG 561 as an antifogging agent, and showed good blocking resistance, mechanical strength and fogging presentation (45° C. water for 45 days or 0° C. environment and 20° C. water for 24 hours).

Other agricultural antifogging films, such as the ones disclosed in JP Pat. 09-95,545, were prepared using olefin copolymer compositions containing sulfonated olefin copolymers, ethylene-$C_{3-12}$ olefins, and ethylene-acrylic copolymers. The olefin copolymers were synthesized by polymerization of olefins in the presence of metallocene (Zr) catalyst containing silica and methylaluminoxane. More specifically, a transparent antifogging film was prepared from a mixture of 80% sulfonated olefin polymer (reaction product of butane sulfonate with ethylene-acrylic copolymer) and 20% of ethylene-hexene-1 copolymer which was polymerized in the presence of a catalyst system containing silica, methylaluminoxane, bis(1,3-n-butylmethyl cyclopentadienyl)zirconium dichloride and tri-isobutylaluminum.

JP Pat. 09-77,938 discloses a polymer composition with good sliding properties that comprises 10–60% of graft copolymers manufactured by grafting an elastomer with $\geq 1$ layers of antifogging agent KFG 561. The resultant laminate used ethylene-vinyl alcohol copolymer as a middle layer, 20% of hydrogenated butadiene-styrene elastomer as an inner layer, and 10% of the said elastomer outer layer comprises a fire retardant agent and showed good blocking resistance, mechanical properties, dust, and fogging presentation.

Fluoropolymer films with wetting $\geq 35$ dyn cm, as disclosed in JP Pat. 09-136,980, were mixed with antifogging agents comprising water-thinned acrylic polymer emulsions, such as ethyl acrylate-2-hydroxyethylmethacrylate-2-hydroxymethacryloxybenzophonone-methyl methacrylate copolymer, and colloidal $SiO_2$. Films prepared according to this patent showed reasonably good antifogging property for 7 months.

Two Japanese patent inventions, JP Pat. 09-165,178 and JP Pat. 09-165,447, disclose heat-aging and light-resistant propylene polymer compositions causing no fogging of glass for use in automotive interiors. These compositions contain (A) crystalline polypropylene, (B) inorganic filler, such as $TiO_2$, (C) ethylene-propylene elastomer, and (D) conventional stabilizers, antioxidants, antiblocking agents, and other additives such as epoxy resins, hydroxyl-containing low molecular weight polyolefins, polyethylene waxes, and anionic surfactants. Plates prepared from this composition by kneading, pelleting, and injection molding show 150° C. oven life for 320 hours. The plate and glass plate were left in a sealed container at 120° C. for 20 hours and showed a haze of the glass of 0.8%.

In another patent entitled "Fog-Resistant Heat-sealable Film", U.S. Pat. No. 4,341,825, there is disclosed a transparent, heat-sealable, laminated film that has a first layer of a difficulty heat-sealable polymer, such as an axially oriented polyethylene terephthalate film with 0.002–0.006 cm thickness, and a second layer of a readily heat-sealable polymer, such as low density polyethylene and copolymers of ethylene with acrylic acid, ethyl acrylate and vinyl acetate, chemically interfacially joined to the first film layer. The said second film layer comprises 0.2–0.7% of an alkyl phenyl polyethylene glycol ether of the formula, R—$C_6H_4$—O—$(CH_2)_n$OR'—OH, where R-alkyl $C_{10\text{-}15}$ and alkylene $C_{4\text{-}10}$ as an antifogging agent. The resulting laminated film is then heated to 130° C. and exposed to UV-light through the second film layer for a time and at an intensity sufficient to cause the formulation of the chemically interfacial bond between the two layers. The film obtained resists the formation of fog when utilized to package refrigerated foods. However, the disadvantages of this invention can be noted as the following: (1) the subject film comprises two layers containing non-oriented ethylene polymers, (2) the subject film has a high thickness, (3) the subject film has a high content of antifogging agents as compared with more conventional polymer fog-resistant films, and (4) the antifogging agents used in the subject film were synthesized by reaction of alkyl phenol with polyethylene oxides. In this case, the trace of the phenol will be present in the product synthesized. This can limit the use of this specific additive in the food packaging industry.

Another patent, entitled "Fog-Resistant Olefin Polymer Films", U.S. Pat. No. 4,486,552, discloses a film-forming composition for making packaging films that are resistant to fogging, especially when employed as a packaging film for moist products. The subject film of this patent comprises an ethylene polymer, especially a linear low density polyethylene, and 0.5–2.0% of antifogging agents, such as an ethoxylated alkyl phenol along with a mixed mono-, di-, and/or triglyceride, a polyoxyalkylene fatty acid ester or various combinations of said additives. The mixing of the antifogging agents into the ethylene polymers, which can be LDPE, LLDPE, HDPE, ethylene-octene-1, or blends or alloys of said olefin polymers, is done by mixing the antifogging agents into molten polymer by commonly used techniques, such as roll-milling, mixing in a Banbury type mixer, mixing in an extruder barrel, or the like. The subject film was formulated as 0.015 mm on a cast film unit at 260° C. melt temperature and chill roll temperature of 18° C. It is noted that the films prepared according to this patent have a relatively high fog resistance when compared with commercially available plasticized poly(vinyl chloride) films, such as the one disclosed in U.S. Pat. No. 4,072,790. Further, other high qualities are produced, such as improved transparency (64.3 against 5.0 for PVC), gloss (95.9 against 89.0), haze (1.0% against 2.0%), lower heat seal range (121–127° C. against 149–177° C.), and overall toughness, as compared to PVC films. However, it was shown that the antifogging agents used in this patent exude to the surface of the film within approximately 48 hours after fabrication. The subject films of this patent have the following disadvantages: (1) the films are not multi-layered and biaxially oriented, (2) the films have a high thickness and high density resulting in a low yield, (3) there is a low heat-sealing temperature, (4) there are low values of surface and mechanical characteristics, the film surfaces are not treated by corona discharge, and (5) the film comprises relatively high concentrations of antifogging agents used in the polymer composition.

U.S. Pat. Nos. 4,876,146 and 4,956,209, disclose "Antifogging Multi-layered Film and Bag Produced Therefrom for Packaging Vegetables and Fruits". These patents describe biaxially oriented and multilayered antifogging polyolefin films useful for packaging fresh vegetables and fruits comprising: (A) a 4–100 µm base layer formed from polypropylene or ethylene-(5%)-propylene copolymer or ethylene-vinyl acetate (acrylic acid or styrene) copolymer; and (B) one or two surface layers that are 0.3–8.0 µm thick and having heat-sealable properties resulting from a (1:1) mixture of propylene-butene-1 (18%) and ethylene (3.5%)-butene-1 copolymers containing 0.3–3.0% antifogging agent such as higher fatty acid ester of monoglyceride (or alkyldialcoholoamide, polyalkylene glycol, polyalkylene glycol alkylphenol ether). There are also other conventional additives, such as antistatic and lubricating agents. In accordance with said patent it is possible to incorporate the antifogging agent only in a base layer of the film so that the antifogging agent migrates to and diffuses into the surface layer(s) after laminating the layers. This migration and incorporation of the antifogging agents into the surface layers provides the antifogging property important to the surface layer. Antifogging properties were observed, the film was formed as a bag and "Shtitake" mushroom were enclosed in the bag; the temperature was varied twice per day with a rise and drop between 20 and 40° C.; the result was observed after 1 day. There was little fogging, discoloration, and the measured surface tensions were 38–42 dyne/cm. The disadvantages of the films prepared in accordance with said patent included: (1) high values of haze (3.1%), (2) low values of sheen (86.6%), (3) coloring agent in the film does not comply with food contact standards of the U.S. FDA, (4) the identification of fogging properties used a non-effective method, (5) the films had low performances as antifogging surfaces, i.e. discontinuous film of water is observed on the surface, (6) E-P-B terpolymer is not used in the surface layers, (7) ethylene-vinyl acetate copolymers are used in the base layer and most probably for improvement of barrier properties of films, and (8) present patent is limited to using 2–3 layered films. U.S. Pat. Nos. 4,876,146 and 4,956,209 which are hereby incorporated by reference.

All of the patents previously mentioned above, however, suffer from not having antimicrobial properties.

In the recent years, essentially growing trend is the use of various bioactive agents, including predominantly ecologically pure metal-containing biocides in polymer production industries for preparation of antimicrobial, antibacterial and antifungal polymer materials such as films, sheets, coatings, plastics, fibers, composites, etc. The number of patent publications in this field have increased in recent years. The following references have attempted to address antimicrobial films:

(1) U.S. Pat. No. 4,938,955, 1990 discloses an antibiotic resin composition comprising at least one antibiotic zeolite of which ion-exchangable ions are partially or completely replaced with ammonium ions (5–15%) and antibiotic metal ions ($Ag^+$ of 1–15%), at least one discoloration inhibitor such as benzotriazole, oxalide, anilide, salicylic acid, phosphous, sulfur, etc. compounds and at least one polymer resin (this composition exhibits antibiotic property and does not discolour with time, and can be employed to form a variety of products which require antibacterial and/or antifungus properties);

(2) Transparent bactericidal multilayer sheets with haze <5% comprise a crystalline thermoplastic resin containing 0.05–5 phr granular zeolite containing bactericidal metal ions in a sheet comprised polypropylene containing 0.5% Bacterikiller BM 103 (zeolite A containing 3.5% Ag) [JP Pat. 04,275,142 (1992), Chisso Co., Japan]; (3) Antibacterial polyolefin compositions with inhibiting effects on the growth of bacteria and moulds contain polyolefins and 2-pyridinethiol 1-oxide and its metal (Zn) salts or other organic biocides (polypropylene 100, 2-(4-thioazolyl) benzimidazole 0.25 and Zn 2-pyridinethiol 1-oxide 0.25 part were roll kneaded at 230° C. and then hot pressed at 220° C. to give a 2 mm sheet, which completely inhibited of the growth of Aspergillus niger, Penicillium citrinium, Chaetomium globosum, Aurebasidium dulllans, and Gliocladium virens at 28° C. for 28 days) [JP Pat. 04,270,742 (1992), Shinto Paint Co. Ltd., Japan]; (4) Antibacterial heat-resistant polyolefin compositions comprising polyolefins (polypropylene) 100, bactericidal metal ions (Ag, Cu, Zn and/or Sn ions supported on zeolites) 0.01–1.5, dimethylsiloxane oil 0.01–0.2, and aluminium borate whisker ($9Al_2O_3 \cdot 2B_2O_3$) 0.01–0.1 part showed good antibacterial action as tested against colon bacilli [JP Pat. 04,363,346 (1992), Tonen Kakagu Kk., Japan]; (5) JP 04,13,733 (1992) discloses antibacterial films for packaging chemicals and food which were prepared by treating one or two surfaces of films containing aluminosilicic acid salts with electrical corona (a composition containing 2 parts zeolite A (Ag content 6.7%, $NH_4$ content 0.5%) and polyamide (6-nylon 66 copolymer) were together extruded and exposed to electrical corona for 0.2–10 s to give an antibacterial film with good adhesion to ham, versus poor adhesion for the film not treated with said corona); (6) U.S. Pat. No. 5,614,568, 1995 (Mawatari, M., et al., Japan Synthetic Rubber Co., Ltd., Tokyo) claimed an antibacterial resin comprising (A) 100 parts by weight of aromatic alkenyl resin, specifically styrene resin, (B) 0.01–30 parts of an inorganic metal compound or a porous structure substrate which has been injected to ion-exchange with a metal ion selected from the group consisting Ag, Zn, Hg, Sn, Pb, Cd, Cr, Co, Ni, Mg, Fe, Sb and Ba, and (C) 0.01–30 parts of a polyethylene comprising —COOH, —COOM(salts), —OH, —COOR, and epoxy, anhydride and amine functional groups, a polypropylene comprising said selective functional groups with molecular weight 10000–30000; (7) Japan Chem. Ind. Co. (JP Pat. 09,176,370, 1997) discloses an antimicrobial injection-moldable polypropylene composition showing no discoloration or degradation during processing, storage and uses contain 0.2 phr of liquid paraffin, 1.0 phr of the mixture of inorganic compounds $Ag_{0.15}Na_{0.5}H_{0.35}$, $Zr_2(PO_4)_3$ and $Mg_{0.7}Al_{0.3}O_{1.15}$ which was used as an antimicrobial agent; (8) Polyethylene terephthalate films coated with thin Ag, Cu and Ti-layers by sputtering treatments have high antibacterial activity. The reducing in bacteria values of almost 100% were determined by the SEK Shake Flask Method and the Contacted Film Method [S. Kubota, et al, *Bakin Bobai,* 25 (7), 393 (1997); *Chem. Abstr.,* 127, 122386s (1997)]; (9) Tokuda, et al, [JP Pat. 09,136,973, 1997] describes bactericidal packaging films comprising thermoplastic resins or blends on the base of PE, PP, PVC, polyesters and/or PS and calcined powder ceramics containing 40–60% of $SiO_2$, 20–30% of $Al_2O_3$, 4–8% of ZnO, 2–5% $TiO_2$ and 0.1–1.0% Ag or Cu salts as an antibacterial agent (these films were prepared by mixing above ceramics with said polymers and forming into films or by spreading or printing above ceramic-containing resins on resin base films); (10) JP Pat. 09,123, 264 (1997) discloses antibacterial decorative sheets and manufacture of decorative moldings (these sheets were prepared by shaking colored base sheets with thermosetting diallyl phthalate resin composition containing 0.5% of Ag/Zr phthalate, Ag tripolyphosphate, Ag hydroxyapatite, and/or $(Ag/Ca)_3$ phosphate. A printed paper sheet was hot pressed with a moldable polymer composition to form a waterproof pan for bathroom uses); (11) Bactericide-containing abrasive agents and resin moldings for video and arcade games comprise a thermoplastic resin (98% of polycarbonate) incorporated with fillers (1%) and bactericides (Ag-containing zeolite, Bactekiller) or bactericide-treated powders (1%) [Sumitomo Elect. Ind. Ltd., JP Pat. 09,77,880, 1997]; (12) JP Pat. 09,77,042 (1997) releases to antimicrobial synthetic resin containers for preserving drinking water (this container is prepared using synthetic resins with Ag-containing glass particles that release adequate amount of microbiocidal silver ions ($Ag^+$) into the water where growth of bacteria or fungi in the drinking water is prevented by these ions); (13) JP Pat. 09,002,517, 1998 [Taisho Pharmaceutical Co. Ltd. (Tokyo, Japan)] discloses a process for making a bottle and cap with antibacterial properties on their inner contact surfaces. Antimicrobial zeolite power (1 to 5% by weight) containing microbiocidal Ag, Zn and Cu ions is mixed with thermoplastic resins such as ethylene-vinylacetate copolymer, polypropylene and polyethylene (the zeolite is dispersed throughout the bottle and is present on both inner and outer surfaces and can also be used for both cap and membrane seal); (14) Polypropylene plastic table wares contain an antimicrobial agent (Amenitor) (JP Pat. 09,108,084, 1997); (15) Bactericide power (Bactekiller) or bactericide-treated power containing adhesive agent and resin moldings for video areade games were described (*Chem. Abstr.*, 127, 35460t, 1997); (16) Silver (Ag)-zeolite antimicrobial agents for protection of the plastic films from various microorganisms were manufactured by Michubusi Co. Bactericide ceramic power containing 0.1–1.0% Ag or Cu, 2–5% $TiO_2$, 4–8% ZnO or $MnO_2$, 20–30% $Al_2O_3$ and 40–60% SiC or $SiO_2$ was recommended to use in the various thermoplastic composition (polyolefin, polystyrene, polyesters, etc.), resins and binders [T. Ishitaki, *High Polym. Japan*, 39(10), 744 (1990); Y. Kajiura, *Jidosha Gijutsu*, 51(5), 34 (1997); JP Pat. 09,136,973 (1997)]; (17) Antimicrobial activities of some new coordination polymers were also described by Patel, et al. [B. Patel and M. Mohon, *J. Polym. Mater.*, 13(4), 261 (1996)].

However, all these publications are related to the preparation and use of various antimicrobial polymer materials including non-orientated and non-multilayered polymer films, sheet, etc. containing bioactive metal ions. Thus the above patents describe inventions are essentially different from the present patent invention which is concerned with preparation of semi- and biaxially oriented and multilayered antimicrobial thin films containing $Ag^+$-containing polymeric bioactive agent only in the skin layer and having high physico-mechanical, thermal and antimicrobial properties. Another distinctive feature of these films is possibility of their use in the food packaging applications, where antifogging properties are required.

Several Firms such as Taisho Pharmaceutical Co. Ltd. (Tokyo, Japan), Kanebo Chemical Industries, Ltd. (Osaka, Japan), M. A. Hanna Company (USA, Neutrabac™ Antibacterial Masterbatch), Wells Plastic Ltd. (Staffordshire, UK), etc. have already started to manufacture organic and inorganic antibacterial agents and various antimicrobial Masterbatches for use in thermoplastic polymer compositions.

Many organic and organoelement compounds having high biological activities are also used in polymer film-forming composition systems [Z. M. Rzaev, *CHEMTECH*, (1),58 (1976); Z. M. Rzaev et al., England Pat. 1,270,922 (1972); U.S. Pat. No. 4,261,914 (1981); U.S. Pat. No. 4,314,851 (1982); Z. M. Rzaev et al.,*Bioresistant Organotin Polymers*, Chemistry, Moscow, 1996 (RUSs.)]. Thus, (1) "ICI Biocides" Firm (UK) prepared and patented new water soluble biocides on the base of isothioazolione useful for the effective preservation of polymer resins, specially aqueous-based paints from bio-destruction with microorganisms in the stage of synthesis, storage and uses of these materials [C. L. P. Eacoff, *Orient. J. Oil and Colour Chem. Assoc.*, 74 (9), 322 (1991)]; (2) Polen Kagaku Sangyo K.K. [JP Pat. 09,169, 073, 1997] discloses antibacterial and antifungal sheets laminated with low expanded olefin polymer (such as HDPE) compositions containing 0.1–1.0% 2-(4-thioazolyl) benzimidazole as an antibacterial and antifungal agent showing good deep drawability; (3) Antimicrobial rubber articles contain ammonium salt of chlorohexidine as an antimicrobial agent [UK Pat. 8,919,152 (1990)]; (4) Biocide Cl-containing polyketones having antibacterial activity against selected yeast, fungi, and bacteria were prepared by Fiedel-Graft [Friedel-Craft] reaction of o-cresol with chloroacetyl chloride, dichloromethane and dichloroethane in the presence of anhydrous $AlCl_3$ as a catalyst in nitrobenzene as solvent [B. T. Petel, et al, *Orient. J. Chem.*, 13 (1), 83 (1997); *Chem. Abstr.*, 127, 136122q (1997)]; (5) Polyethylene four-layered film was coated with mixture of allyl isothiocyanate (as a biocide), polyfunctional isocyanate, polyols and dibutyltin laurate (as a catalyst) to give a multilayered film with polyethylene outer layer having antibacterial activity [JP Pat. 09,151,317, 1997]; (6) Matsukawa Electric Works, Ltd. (Japan) was disclosed a method of preparing plastic table wares (plastic bowl) containing antimicrobial agents (Amenitop) by moulding. The core potion is formed with a polypropylene resin and this is coated with another polypropylene containing a said antimicrobial agent; (7) Kyowa Co. Ltd. [JP Pat. 09,135,716, 1997] patented the gas-permeable and antimicrobial bags for the medical application. These bags were prepared from cushion bases consisting open-celled polymer foams and bactericide-containing hydrophobic noncircular fiber; (8) p-Hydroxy butylbenzoate [JP Pat. 63,173,723 (1988)], 2-(4'-thiazolyl)-benzimidazole [U.S. Pat. No. 4,008,351 (1977)], Pt-vinylsiloxane complex [JP Pat. 04,202,313 (1993)], polymeric iodine complexes [U.S. Pat. No. 3,907,720 (1975), phosphate esters [U.S. Pat. No. 3,888,978 (1975), U.S. Pat. No. 3,991,187 (1976), U.S. Pat. No. 4,661,477 (1987), U.S. Pat. No. 4,935,232 (1990)] and 2,3,5,6-tetrachloro-methylsulfonylpyridine (for preparation antibacterial styrene type resin compositions) [JP Pat. 07,82,440 (1995)] have also been recommended for use as bactericide and antimicrobial agent in the various polymer compositions, film and sheets.

There are a number of patents disclosing various polymer composites, thermoplastic fibers, sheets, coatings, films, etc. having biological activity toward different type of microorganisms [Shima et al., U.S. Pat. No. 4,000,102, 1976; Dell et al., U.S. Pat. No. 4,584,192, 1986; Fink et al., U.S. Pat. No. 4,751,141, 1988; Gillete et al., U.S. Pat. No. 5,152,946, 1992; Grighton et al., U.S. Pat. Nos. 5,246,659, 1993; 5,104,306, Apr. 14, 1992]. For example, (1) U.S. Pat. No. 5,178,495, 1993 discloses a polymeric film with biocide. A multi-ply film has been developed that includes a biocide in at least one the film layers. Said biocide mixed with the thermoplastic prior to extrusion of the sheet. This sheet with biocide can be used to construct water containment facilities for drinking water, fish farms and industrial use and can be used as a covering for water tanks or equipment in environments that promote microbial growth at the surface of the film; (2) U.S. Pat. No. 5,777,010 1998 (Nohr R. S., et al., Kimberly-Clark Worldwide, Inc., Neenah, Wis.) discloses melt-extrudable composition containing antimicrobial siloxane quaternary ammonium salts. These compositions which includes a thermoplastic polyolefin and a siloxane quaternary ammonium salt additive. Upon melt extruding the thermoplastic composition to form fibers and non-woven webs, or other shaped artides, the surfaces of such shaped articles exhibit antimicrobial properties. (3) Early, antimicrobial siloxane quaternary ammonium salts were patented [U.S. Pat. No. 5,567,372, 1994 and U.S. Pat. No. 5.569,732, 1994] and published [Nohr R. S., et al., *J. Biomed. Sci., Polym. Ed.*, 5(6), 607 (1994)] (U.S. Pat. No. 5,567,372, 1994 discloses a method of preparing a non-woven web containing antimicrobial siloxane quaternary ammonium salts); (4) U.S. Pat. No. 5,527,570 [Addeo, A., et al.,1996, Centro Sviluppo Settori Impiego SRL, Milan, Italy)] relates to a multilayer and multifunctional packaging elements having high-absorption activity toward aqueous liquid substances as well as barrier properties toward gases such as oxygen and carbon dioxide are prepared by thermoforming (Each layer comprises a polymeric thermoplastic material. Intermediate layer of this packaging element may also contain antibacterial agents); (5) U.S. Pat. No. 5,142,010, 1992 (Olstein, A. D. et al., H. B. Fuller Licensing & Financing Inc., Wilmington, Del.) discloses polymeric biocidal agents containing carboxyl groups, fluorene substitute and alkyl $C_{1-20}$ groups, and any bioactive naturally occurring aminoacid chain (the resulting polymers are disclosed to be useful in any variety of applications requiring an antimicrobial agent or an active sanitizer or disinfectant including films, coatings and adhesives, as well as also being useful in medial, food preparation and personal care product applications; (6) Describes an antimicrobial film-forming compositions containing bioactive polymers (homo-, co- and terpolymers of monomers containing pyran groups) having pendant pyran groups [Greenwald R. B. et al., U.S. Pat. No. 5,108,740, 1992, Ecolab Inc., St. Paul, Minn.] (this publication describes a liquid composition that yields an abrasion resistant polymeric film on a surface that provides extended protection from microbial growth through slow release of a potent antimicrobial agent).

As evident from the above described patent publications, there is relatively small number of patent publications describing polyolefin based, in particular, mono- and biaxially oriented polyolefin based films, and all of patent publications suffer from one or more of the following properties: not being multilayered and oriented polyolefin non-opaque films, not being heat-sealable; not having antimicrobial properties using thin films containing $Ag^+$-containing polymeric bioactive agent only in the skin layer, not having antifogging properties.

SUMMARY

It is an object of the present invention to design and prepare a multilayer structure (having at least an antifogging and antimicrobial skin layer (A)/a core layer (C)/an outer layer (E) structure) for semi and biaxially oriented polyolefin based antifogging films having advantageous properties as compared with known and commercial films such as low values of haze, high values of sheen, lower longitudinal and transverse shrinkage, which provides high dimensional stability, and excellent antifogging and antimicrobial properties. Preferably the antifogging and antimicrobial skin layer (A) is electrical corona or flame treated. Electrical corona or flame treatment of the the outer layer (E) may enhance ink anchorage and increase the printability of this layer. Preferably, the films comprise an inner (B) layer between the antifogging and antimicrobial skin layer (A) and the core layer (C). More preferably, the inner (B) layer has the same composition as antifogging and antimicrobial skin layer (A) without the antimicrobial additives. Preferably, the films may comprise a second inner (D) layer between the outer (E) layer and the core layer (C). More preferably, the second inner (D) layer has a preferred composition of 100 percent (%) E-P-B terpolymer.

Antimicrobial and antifogging $\geq 3$ layers polymer films with preferable A/C/E structure useful for the food, medicine and agriculture applications as well as for other general packaging and non-traditional special applications. More preferably, antimicrobial and antifogging films having a A/B/C/E structure. Most preferably, biaxially oriented polypropylene films having symmetrical structure A/B/C/D/E, where two outer layers A and E are having antimicrobial and antifogging properties and heatsealable and two intermediate layers B and D are made of E-P random copolymers or E-P-B terpolymers, with or without antifogging agents.

A preferred embodiment of antifogging and antimicrobial skin layer (A) comprises the following compositions: polypropylene greater than or equal to 1 percent (wt. %), E-P-B terpolymer or E-P random copolymer greater than or equal to 70 percent (wt. %), a mixture of glycerol monostearate (GMS) and diethanolamine (DEA) greater than or equal to 0.2 percent, special additive greater than or equal to 0.1 percent, an antiblocking agent greater than or equal to 0.2 percent (wt. %) of synthetic silica or zeolite and an antimicrobial agent greater than or equal to 0.1 percent (wt. %) of $Ag^+$-containing inorganic polymer of linear structure. More preferably, each component of skin layer (A) has a percentage in the following ranges (the total of all components for any specific embodiment would, however, equal 100 percent (wt. %)): polypropylene between 1 and 5 percent (wt. %), E-P-B between 90 and 98 percent (wt. %), a mixture of GMS and DEA between 0.2 and 0.5 percent (wt. %) where the GMS concentration in the mixture may vary from 1% to 99%, and special additive (a mixture of higher fatty acid ester of polyvinyl alcohol or polyether polyol, where respective ratios may vary from 1% to 99%) between 0.1 and 0.5 percent (wt. %) and an antiblocking agent between 0.1 and 0.25 percent (wt. %) of synthetic silica, polymethylmetacrylite or zeolite and an antimicrobial agent between 0.2 and 1.0 percent (wt. %) of $Ag^+$-containing inorganic polymer of linear structure.

Preferably, inner layer (B) has the composition totals: polypropylene greater than or equal to 1 percent (wt. %), E-P-B terpolymer or E-P random copolymer greater than or equal to 70 percent (wt. %), and a mixture of glycerol monostearate(GMS) and diethanolamine(DEA) greater than or equal to 0.2 percent, special additive greater than or equal to 0.1 percent, More preferably, each component of antifogginner layer (B) has a percentage in the following ranges (the total of all components for any specific embodiment would, however, equal 100 percent (%)): polypropylene between 1 and 5 percent (%), E-P-B between 90 and 98 percent (%), a mixture of glycerol monostearate(GMS) and diethanolamine(DEA) greater than or equal to 0.2 percent, special additive greater than or equal to 0.1 percent, an antiblocking agent greater than or equal to 0.2 percent (wt. %) of synthetic silica. More preferably, each component of antifogging inner layer (B) has a percentage in the following ranges (the total of all components for any specific embodiment would, however, equal 100 percent (%)): polypropylene between 1 and 5 percent (%), E-P-B between 90 and 98 percent (%), a mixture of GMS and DEA between 0.2 and 0.5 percent (wt. %) where the GMS concentration in the mixture may vary from 1% to 99%, and special additive (a mixture of higher fatty acid ester of polyvinyl alcohol or polyether polyol, where respective ratios may vary from 1% to 99%) between 0.1 and 0.5 percent (%) and an antiblocking agent between 0.1 and 0.25 percent (wt. %) of synthetic silica or zeolite. This inner layer does not have antimicrobial agent.

In a preferred embodiment, second inner Layer D has a preferred composition of 100 percent (%) E-P-B terpolymer or E-P random copolymer Further, outer layer E has the same preferred and more preferred compositions as either of layers A or D.

Finally, a preferred embodiment of core layer C comprises the following compositions (the total of all components for any specific embodiment would, however, equal 100 percent (%)): polypropylene greater than or equal to 95 percent (wt %), a mixture of GMS and DEA, would be greater than or equal to 0.2 percent (wt %) and special additive equal or greater than 0.1 percent (wt %) More preferably, each component of layer C has a percentage in the following ranges: polypropylene between 97.5 and 99.5 percent (wt.

%), a mixture of GMS and DEA between 0.2 and 0.5 percent (wt. %) where the GMS concentration in the mixture may vary from 1% to 99%, and special additive (a mixture of higher fatty acid ester of polyvinyl alcohol or polyether polyol, where respective ratios may vary from 1% to 99%) between 0.1 and 0.5 percent (wt. %)

Antifogging and $Ag^+$-containing antimicrobial biaxially oriented polypropylene (BOPP) films, can be prepared by using the tandem extruder system with two extruders supplied with two, three or four satellite co-extruders, flat die, chill roll, corona discharge (onto the skin layer or, alternatively, both the skin layer and the outer layer) and recycling line as well as the mono- and semi-oriented cast film technology with temperature controlled mold. After mono- and biaxially stretching (4–7 times at 105–140° C. in the machine direction, MD and 7–11 times at 150–190° C. in the transverse direction, TD) and air corona discharged of one outer surface in the given conditions. Preferably, the antifogging and antimicrobial films have the following characteristics: specific density of 0.91 $g/cm^3$, low haze around 1.5% (+−0.2), high gloss greater than or equal to 95%, heat sealability around 120° C., excellent dyne level retention (preferably equal or greater than 40 dynes/cm) for good printability and antifogging characteristics, excellent antifogging properties (rated 'E' according to ICI's cold fog test method, which means that the antifogging surface of the film is almost free of big water droplets which makes it invisible) and excellent antimicrobial activity (99.9%) toward various microorganisms, especially and preferably against three common bacteria *Staphylococcus aureus, Escherichia. coli* and *Salmonella enteritidis*.

One the other hand, this invention also provides longer shelf life for the freshcut and pre-packed vegetables, salads, fruits and like, due to the high biological activity of the antimicrobial agent which prevents the certain bacteria's growth. Another advantage of the present invention is the easy processability of the antimicrobial agent whose processing conditions are within the processing windows of the ingredients put in the conventionalal or antifogging BOPP films. In fact this advantage is provided by the high thermal stability of the antimicrobial agent which is >300° C. and which is well above of the operating temperatures of the raw materials present in BOPP or antifogging BOPP films. In other words, under normal processing conditions of BOPP film manufacturing, the said antimicrobial agent does not show chemical degradation or decomposition.

Another important advantage of the present invention is the high degree of antimicrobial performance against the certain bacteria by using only a very low concentration of antimicrobial agent, due to its usage only in the very thin layer(s). This very low concentration of antimicrobial agent in the polymer matrix is preferably 30 times lower, as compared with conventional biocides used in known polymer compositions, due to its only use of a thin antifogging and antimicrobial skin layer (A), preferably between 0.5–1.5 $\mu$m. The usage of so low concentration of antimicrobial agents advantageously reduces the cost of the film.

Another aspect of the present invention is the possibility to production of the films in the form of mono-oriented and biaxially oriented multilayer thin films with similar component and layer compositions by using cast film technology and tandem extruder system technology, respectively. According to the present invention the technological aspects of manufactured process of said films are (1) multilayered and mono-oriented cast film technology and (2) tandem extruder system technology by the fact that tandem extruder system with two main extruders for better homogeneity and dispersion of the raw materials, supplied with three satellite co-extruders, recycling line and corona discharge. The process is carried out by three chill-roll or water bath treatments and two step of longitudinal orientation allowing to prepare good homogenized film with matte appearance having improved surface properties and dimensional stability. The skin layer or, alternatively both the skin layer and the outer layer, of biaxially oriented films prepared may be treated in a known manner by flame or more preferably, by electrical corona discharge. The use of said recycling line for film waste forming in the transverse stretching stage allows to lower film cost For example (as a preferred, but not the only embodiment of the process), after coextrusion, an extruded five-layer film is taken off over the corresponding process steps through a chill roll and cooled, and cast film profile is controlled by β-Gauge equipment. The film is subsequently stretched longitudinally at two steps and stretched transversely. After biaxially orientation, the film is set and electrical corona-treated on one or two sides. The following conditions are preferable: (1) Extrusion: extrusion temperature 170–260° C., first chill roll temperature 10–45° C.; (2) Machine (longitudinal) stretching: stretching roll temperature of first step 105–120° C. and second step 115–140° C., longitudinal stretching ratio 4:1–6:1 for first step and 1:1-1:2 for second step; Transverse stretching: temperature of heat-up zones 150–185° C., temperature of stretching zones 155–185° C., transverse stretching ratio 7.5:1–11:1; Recycling: edges of the biaxially orientated film is recycled and fed to the line again; Setting: setting temperature 165–185° C.; electrical corona discharge (A side only or alternatively both A and E sides, together): voltage 10–25 kV and frequency 1.5–30 kHz. The following preferable conditions for the multilayered mono-oriented (in MD only) antimicrobial films in accordance with cast film technology in detail are selected: (1) extrusion temperature 250° C. by using temperature controlled MITSUBISHI type die, (2) chill roll temperature 10° C. (3)film profile is controlled by β-Gauge equipment, (3) the speed of film production line 100 m/min, and (4) level of air corona discharge on A surface of the film is 11 Kw It is further object of the present invention to widen the field of application of said films useful for the food, medicine and agriculture applications as well as for other general packaging and non-traditional special applications including bioprotection of food contacting materials and food handling areas, medicine devices, agriculture products as well as applications in potential areas like food-storage containers, in oral hygienic products, hospitals and other health institutions to provide hygienic conditions, for preserving drinking water and as a covering for water tanks, etc.

Another aspect of the present invention is to use new systems of additives, i.e.—a mixture of GMS and DEA, special additive (a mixture of higher fatty acid ester of polyvinyl alcohol or polyether polyol) as antifogging agents, in combination with the antimicrobial agent $Ag^+$, to create dual-effect polymeric films having both antifogging and antimicrobial properties.

Those additive systems are used with the following compatible polyolefins selected from polypropylene, a propylene-ethylene random copolymer, propylene-butene-1 random copolymer or an ethylene-propylene-butene-1 terpolymer with various compositions, where the last three are used for the heat sealable skin layers.

Advantages of antifogging and antimicrobial films are: (1) Antimicrobial activity against certain bacteria, (2) excellent antifogging properties (3) high antimicrobial performance in comparative low concentration of antimicrobial agent, (4)

preservation of antimicrobial activity during the long time of storage. of the polymeric films, even after corona or UV-treatment, (5) low total migration properties with the diluents distillated water, acetic acid, ethyl alcohol, heptane and olive oil as mentioned in the directives of EEC and FDA allowing to use of these films in food packagings, (6) high optical properties (low haze, high sheen), (7)high physical-mechanical properties (8) possibility of use various thermoplastic film-forming polymers in core layer of films, and (9) wide range of conventional and special application fields of invented films.

DESCRIPTION

The present invention is an antifogging and antimicrobial film that is a multi-layered, oriented and made from polyolefins (polypropylene (PP), propylene-ethylene random copolymers, ethylene-butylene random copolymers and/or ethylene-propylene-butylene (E-P-B) terpolymers with various contents of E- and B- units). The present invention is useful for food packaging, food-wrapping, agricultural and horticultural applications, or any application where there is any condensation of water vapor on the various surfaces in the form of droplets and effectiveness of certain bacteria needs to be reduced.

The following Examples of the present invention for preparation of multilayered antifogging and antimicrobial films with different composition, properties are illustrated.

EXAMPLE 1

A first example of a multilayer film (A/C/E) having antifogging and antimicrobial properties comprises: (A) 1.0 $\mu$m antifogging and antimicrobial skin layer containing 92.25% by weight of said ethylene-propylene-n-butylene-1 terpolymer with given composition (ethylene [$C_2$]=1.5–4.5%, n-butylene-1 [$C_4$]=3.0–15.0%), 0.25% by weight of zeolite as an antiblocking agent, 6.0% by weight of polypropylene homopolymer, and 1.0% by weight of $Ag^+$—as an antibacterial and antimicrobial agent (in derived from a masterbatch having 20% active agent-$Ag.^+$, in a polypropylene carrier: the active is a "silver containing glass powder", this has the CAS No: 65997-17-3, EINECS No: 266-046-0, and EPA, Reg No: 73148 Issue date: 1st Sep. 2000), 0.20% by weight of glycerol monostearate and 0.20% by weight of diethanolamine and 0.10% by weight of special additive (a mixture of higher fatty acid ester of polyvinylalcohol or polyether polyol) as antifogging and antistatic agent, (C) 28.0 $\mu$m core layer (C) from 99.5% by weight of virgin or marked (5-cholesten-3β-ol as a marking agent) polypropylene homopolymer, 0.20% by weight of glycerol monostearate and 0.20% by weight of diethanolamine and 0.10% by weight of special additive (a mixture of higher fatty acid ester of polyvinylalcohol or polyether polyol) as antifogging and antistatic agent and (E) 1.0 $\mu$m outer layer having 99.75% by weight E-P-B terpolymer and 0.25% by weight zeolite. This (E) layer does not exhibit any antifogging or antibacterial property. After biaxially stretching the film (5.5 times at 120° C. in the (longitudinal direction, MD and 8 times at 170° C. in the transverse direction, TD) and electrical corona discharged skin layer (A). Layer (A) has corona treatment in order to accelerate the migration of the antifogging agents and alternatively, outer layer (E) has also corona treatment for further printing purposes.

EXAMPLE 2

A second example of a multilayer film comprises the same thickness structure and composition as in Example 1 with the following changes: the core layer (C) comprises 100% of polypropylene homopolymer.

EXAMPLE 3

A third example of a multilayer film comprises an A/C/E structure but with the following changes in Example 1: the antifogging and antimicrobial skin layer (A) is 1.5 $\mu$m thick, the core layer (C) is 27.0 $\mu$m thick and the non-antifogging, non-antimicrobial outer layer (E) is 1.5 $\mu$m thick. After biaxially stretching, heat setting and corona discharged in the given conditions, that film has antifogging and antibacterial properties on skin layer (A), whereas the outer layer (E) is useful for printing and heat seal applications.

EXAMPLE 4

A fourth example of a multilayer film comprises A/C/E thickness structure and composition as in Example 3 with following changes: Outer layer (E) has also antifogging properties but no antimicrobial property. Thus, outer layer (E) has the same antifogging agents in layer (A) of Example 1 but not $Ag^+$ which provides antimicrobial effect. Film with that structure is produced as described above.

EXAMPLE 5

A fifth example of a multilayer film comprises A/C/E thickness structure and composition as in Example 4 with following changes: Outer layer (E) has the antifogging and also antimicrobial properties where each of layers (A) and (E) are 1.5 $\mu$m thick and have the chemical composition of the skin layer (A) in Example 1. The core layer (C) is 27.0 $\mu$m thick and has the same chemical composition as given in Example 3. This film shows antifogging and antibacterial properties and corona treatment on both sides.

EXAMPLE 6

A sixth example of a multilayer film comprises A/B/C/D/E structure with the following changes in the Example 5: inner layer (B) and second inner layer (D) has the same chemical compositions as skin layer (A) and outer layer (E) where each of the four skin layers is of 0.75 $\mu$m thick. This symmetrical five layered composition provides the same excellent antifogging and antibacterial properties on both sides. Furthermore, the structure of this example also avoids the low output capacity of the single satellite extruders which limits the total output of the manufacturing line by giving high total extrusion output. Corona discharge on each side of this film also gives the flexibility of using either side by converters or packers.

EXAMPLE 7

A seventh example of a multilayered film comprises A/B/C/D structure with following changes in Example 6: the second inner layer (D) becomes the outer layer (E), having the same chemical composition of the layers (A) and (B) but with a thickness of 1.5 $\mu$m. This film exhibits antifogging and antibacterial properties on both sides.

EXAMPLE 8

A eighth example of a multilayer film comprises A/B/C/D/E structure and chemical composition given in Example 6, except the thickness of the core layer (C) which is 32.0 $\mu$m, giving the whole structure 35.0 $\mu$m total thickness.

EXAMPLE 9

A ninth example of a multilayer film comprises A/B/C/D/E structure and chemical composition given in Example 6, except the following changes: inner layer (B) and second inner layer (D) do not have the antimicrobial agent $Ag^+$, and the thickness of the core layer (C) which is 22.0 µm, giving the whole structure 25.0 µm total thickness.

Layer compositions of the above mentioned examples were given in Table: 1 and the physical-mechanical properties of those films were given in Table:2.

Analysis of the initial materials used and films prepared was done according to known standard measurement methods. For example:

Specific density was determined according to ISO 1183 and/or ASTM D-1505. Melt Flow Index (MFI) was measured according to an ASTM 1238/L at 230° C. and under the load of 21.6 N. Melting point (m.p.) was measured by DSC method, maximum point of the melting curve, at a heating rate of 10° C./min. Vicat softening point was determined according to ASTM D-1525. Izod impact strength was measured according to ISO 180/1A. Tensile strength and elongation at break were determined according to ASTM D-882. Haze of the film was measured according with ASTM D-1003. Dynamic friction coefficient of the film was determined according to ASTM D-1984. Sheen of the film was measured according to ASTM D-2103, the angle of incidence was set at 45°. Shrinkage of the film was measured according to ASTM D-2104. The test sample was shrunk at 120° C. for a period of 5 minutes. Water vapor transmission of the film was measured according with ASTM E96. Oxygen permeability of the film was measured according with ASTM D-1434. Surface tension of the film, after surface ionization by electrical corona discharge and after storage for 6 months, was measured according to ASTM D-2578. Antifogging property of the film was evaluated using ICI's the "Cold-Fog" test method (ICI publication 90–6E) for food packaging film.

The "Cold-Fog" test results of the films according to the present invention (E1–E9), and known patented and commercial antifogging films are summarized in Table 3. The test method is as follows: put tap water, 200 ml, in a 250 ml beaker and cover the top of the beaker with a sample of the test film; place the beaker in a temperature controlled refrigerator at 4° C. Observe the appearance of the film for a total period of one week. It was shown that the films of the present invention, as compared with known patents and commercial films have superior antifogging appearance and properties.

The test method used to measure the antibacterial properties of the present invention is a viable count method. An inoculum, which is a nutrient broth containing a known number of bacteria (there should be $10^5$–$10^6$ bacteria in the initial inoculum), is placed directly onto the BOPP film. A piece of standard (not antimicrobial) film is placed over the inoculum to ensure intimate contact between the inoculum and the test film and to prevent the inoculum drying out. The sample is covered with the lid of a petri dish and incubated at 35 deg C. and 90% Relative Humidity (ideal conditions for bacterial growth). After incubation the inoculuni is washed off the sampler, serially diluted and plated out onto Agar plates. These plates are incubated and counts of the still viable (i.e. bacteria able to reproduce and form visible colonies) are counted. Antibacterial test results of the inoculum, commercial film and the film of the present invention are as follows for each tested bacteria type: 1) *Salmonella enteritidis*—Inoculum (initial—$10^6$ bacteria after 24 hrs.—between $10^7$ and $10^8$ bacteria). Commercial Film without Antifogging and Antibacterial Properties (initial—$10^6$ bacteria: after 24 hrs.—between $10^7$ and $10^8$ bacteria), and Film of Present Invention (initial—$10^6$ bacteria: after 24 hrs.—between $10^2$ and $10^3$ bacteria): 2) *Staphlococcus aureus*—Inoculum (initial—$10^6$ bacteria: after 24 hrs.—approximately $10^8$ bacteria). Commercial Film without Antifogging and Antibacterial Properties (initial—$10^6$ bacteria: after 24 hrs.—between $10^8$ and $10^9$ bacteria), and Film of Present Invention (initial—$10^6$ bacteria after 24 hrs.—approximately $10^2$ bacteria): and 3) *Escherichia coli*—Inoculum (initial—$10^6$ bacteria: after 24 hrs.—between $10^5$ and $10^6$ bacteria). Commercial Film without Antifogging and Antibacterial Properties (initial—$10^6$ bacteria: after 24 hrs.—between $10^5$ and $10^6$ bacteria), and Film of Present Invention (initial—$10^6$ bacteria: after 24 hrs.—approximately $10^2$ bacteria).

Food contact approval tests of the present invention also had been done. Accordingly, Global Migration tests of the preferred embodiment film examples described herein have been found in compliance with the following regulations: EEC Regulation 90/128/EEC and amendments (up to and including 99/91/EEC) and FDA Section 21 CFR Ch. 1 175.300 and 176.170. The results for each Food Simulant (Test Conditions, Mean Result) are listed as follows: Olive oil (10 days @40° C., 2.0 mg/dm$^2$). Distilled water (10 days @40° C., 0.2 mg/dm$^2$). 3% w/w Ace.Acid (10 days @40° C., 0.1 mg/dm$^2$). 10% v/v EtoH (10 days @40° C., 0.2 mg/dm$^2$). n-Heptan (30 mins @70° F., 0.9 mg/in$^2$). Distilled water (24 hrs @120° F. $\geq$0.01 mg/in$^2$), and 10% v/v EtoH (24 hrs @120° F. $\geq$0.01 mg/in$^2$).

According to the present invention, the technological aspect of manufactured process of said films is distinguished from known processing by using the tandem extruder system with two main extruders supplied with two or three satellite co-extruders, recycling line and corona discharge. Other processes of manufacturing said films are known to those skilled in the art. The process is carried out by three chill-roll treatments and two steps of longitudinal orientation followed by the orientation in the transverse direction allowing the preparation of good homogenized antifogging films with improved surface properties and dimensional stability. One or both surface of biaxially oriented films prepared are treated in a known manner by corona discharge. After extrusion, the extruded film having at least 3 layers is taken off over the corresponding process steps through a chill roll and cooled, and cast film profile is controlled by B-Gauge equipment. The film is subsequently stretched longitudinally in two steps and stretched transversely. After biaxially orientation, the film is thermally set and air corona treated on one or two sides. The following are typical manufacturing conditions in detail: (1) Extrusion: extrusion temperatures 170–260° C., first chill roll temperature 10–45° C.; (2) machine direction (longitudinal) stretching: stretching roll temperature of first step 105–120° C. and second step 115–140° C., longitudinal stretching ratio 4.5:1–6:1 for the first step and 1:1–1:2 for the second step; Transverse stretching: temperature of heat-up zones 150–185° C., temperature of stretching zones 155–185° C., transverse stretching ratio 7.5:1–11:1; Recycling: edges of the biaxially oriented film is recycled and fed into the line again; Heat setting: setting temperature 165–185° C.; Air corona discharge: 11 Kw.

While these descriptions directly describe the above embodiments, it is understood that those skilled in the art may conceive modifications and/or variations to the specific embodiments shown and described herein. Any such modifications or variations that fall within the purview of this description are intended to be included therein as well. It is understood that the description herein is intended to be illustrative only and is not intended to be limitative. Rather, the scope of the invention described herein is limited only by the claims appended hereto.

TABLE 1

Layer compositions for antifogging-antibacterial films of the present invention.

| Exp | A skin layer | B inner layer | C core layer | D second inner layer | E outer layer |
|---|---|---|---|---|---|
| E1 | 1.0 μm<br>(1)PP-4.02%<br>(2)E(2.5)-P-B(4.5%)<br>Terpolymer-92.25%<br>E-P R.Copo-2.0%<br>(3)GMS-0.20%<br>(4)DEA-0.20%<br>(5)Special Add.-0.10%<br>Zeolite-0.23%<br>Ag+-1.0% | — | 28 μm<br>PP-97.5%<br>GMS-0.20%<br>DEA-0.20%<br>E-P R.Copo-2.0%<br>Special Additive-0.10% | — | 1.0 μm<br>E(2.5%)-P-B(4.5%)<br>Terpolymer 99.75%<br>Zeolite-0.25% |
| E2 | 1.0 μm<br>PP-4.02%<br>E(2.5)-P-B(4.5%)<br>Terpolymer-92.25%<br>E-P R.Copo-2.0%<br>GMS-0.20%<br>DEA-0.20%<br>Special Additive-0.10%<br>Zeolite-0.23%<br>Ag+-1.0% | — | 28 μm<br>PP-100.00% | — | 1.0 μm<br>E(2.5%)-P-B(4.5%)<br>Terpolymer 99.75%<br>Zeolite-0.25% |
| E3 | 1.5 μm<br>PP-4.02%<br>E(2.5)-P-B(4.5%)<br>Terpolymer-92.25%<br>E-P R.Copo-2.0%<br>GMS-0.20%<br>DEA-0.20%<br>Special Additive-0.10%<br>Zeolite-0.23%<br>Ag+-1.0% | | 27 μm<br>PP-97.5%<br>GMS-0.20%<br>DEA-0.20%<br>E-P R.Copo-2.0%<br>Special Additive-0.10% | | 1.5 μm<br>E(2.5%)-P-B(4.5%)<br>Terpolymer 99.75%<br>Zeolite-0.25% |
| E4 | 1.5 μm<br>PP-4.02%<br>E(2.5)-P-B(4.5%)<br>Terpolymer-92.25%<br>GMS-0.20%<br>DEA-0.20%<br>E-P R.Copo-2.0%<br>Special Additive-0.10%<br>Zeolite-0.23%<br>Ag+-1.0% | | 27 μm<br>PP-97.5%<br>GMS-0.20%<br>DEA-0.20%<br>E-P R.Copo-2.0%<br>Special Additive-0.10% | GMS-0.20% | 1.5 μm<br>E(2.5%)-P-B(4.5%)<br>Terpolymer 97.25%<br>E-P R.Copo-2.0%<br>DEA-0.20%<br>Special Additive-0.10%<br>Zeolite-0.25% |
| E5 | 1.5 μm<br>PP-4.02%<br>E(2.5)-P-B(4.5%)<br>Terpolymer-92.25<br>% GMS-0.20%<br>DEA-0.20%<br>E-P R.Copo-2.0%<br>Special Additive-0.10%<br>Zeolite-0.23%<br>Ag+-1.0% | | 27 μm<br>PP-97.5%<br>GMS-0.20%<br>DEA-0.20%<br>E-P R.Copo-2.0%<br>Special Additive-0.10% | E-P R Copo-2.0%<br>Zeolite-0.23% | 1.5 μm<br>PP-4.02%<br>E(2.5)-P-B(4.5%)<br>Terpolymer-92.25%<br>% GMS-0.20%<br>DEA-0.20%<br>Special Additive-0.10%<br>Ag+-1.0% |
| E6 | 0.75 μm<br>)PP-4.02%<br>E(2.5)-P-B(4.5%)<br>Terpolymer-92.25%<br>)GMS-0.20%<br>)DEA-0.20%<br>Special Add.-0.10%<br>E-P R.Copo-2.0%<br>Zeolite-0.23%<br>Ag+-1.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 27.00 μm<br>PP-97.5%<br>GMS-0.20%<br>DEA-0.20%<br>Special Additive-0.10%<br>E-P R.Copo-2.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% |
| E7 | 0.75 μm<br>PP-4.02%<br>E(2.5)-P-B(4.5%)<br>Terpolymer-92.25%<br>GMS-0.20% | 0.75 μm<br>PP-4.02%<br>E(2.5)-P-B(4.5%)<br>Terpolymer-92.25%<br>GMS-0.20% | 27.00 μm<br>PP-97.5%<br>GMS-0.20%<br>DEA-0.20%<br>Special Additive-0.10% | 1.50 μm<br>PP-4.02%<br>E(2.5)-P-B(4.5%)<br>Terpolymer-92.25%<br>GMS-0.20% | |

TABLE 1-continued

Layer compositions for antifogging-antibacterial films of the present invention.

| Exp | A skin layer | B inner layer | C core layer | D second inner layer | E outer layer |
|---|---|---|---|---|---|
| | DEA-0.20%<br>Special Additive-0.10%<br>E-P R.Copo-2.0%<br>Zeolite-0.23%<br>Ag+-1.0% | DEA-0.20%<br>Special Additive-0.10%<br>E-P R.Copo-2.0%<br>Zeolite-0.23%<br>Ag+-1.0% | E-P R.Copo-2.0% | DEA-0.20%<br>Special Additive-0.10%<br>E-P R.Copo-2.0%<br>Zeolite-0.23%<br>Ag+-1.0% | |
| E8 | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 32.00 μm<br>PP-97.5%<br>GMS-0.20%<br>DEA-0.20%<br>Special Additive-0.10%<br>E-P R.Copo-2.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% |
| E9 | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% | 0.75 μm<br>PP-5.02%<br>E(2.5)-P-B(4.5%)<br>Terpolymer-92.25%<br>GMS-0.20%<br>DEA-0.20%<br>Special Additive-0.10%<br>Zeolite-0.23%<br>E-P R.Copo-2.0% | 32.00 μm<br>PP-97.5%<br>GMS-0.20%<br>DEA-0.20%<br>E-P R.Copo-2.0%<br>Special Additive-0.10% | 0.75 μm<br>PP-5.02%<br>E(2.5)-P-B(4.5%)<br>Terpolymer-92.25%<br>GMS-0.20%<br>DEA-0.20%<br>Special Additive-0.10%<br>Zeolite-0.23%<br>E-P R.Copo-2.0% | 0.75 μm<br>PP-4.02%<br>E(2.5)-P-B(4.5%)<br>Terpolymer-92.25%<br>GMS-0.20%<br>DEA-0.20%<br>Special Additive-0.10%<br>E-P R.Copo-2.0%<br>Zeolite-0.23%<br>Ag+-1.0% |

[1] Polypropylene homopolymer having MFI 1.8–3.5 gr/10 min, at 230° C., under 2.16 Kg. Load, mp = 164–166° C.
[2] E-P-B Terpolymer having MFI 5.0–8.5 gr/10 min, at 230° C., under 2.16 Kg. Load, mp = 130–145° C.
[3] GMS: Glycerolmonostearate
[4] DEA: Diethanolamine
[5] Special Additive: Mixture of higher fatty acid acid esters of polyvinyl alcohol or polyether polyol.

TABLE 2

Physical-mechanical properties of the present invention (E1–E9), patented (A), and commercial (B) antifogging films.

| Properties | E1 | E2 | E3 | E4 | E5 | E6 | E7 | E8 | E9 | Patented Films A* | B* |
|---|---|---|---|---|---|---|---|---|---|---|---|
| Total thickness (μm) | 30 | 30 | 30 | 30 | 30 | 30 | 30 | 35 | 25 | 19 | 31 |
| Thickness of core layer (μm) | 28 | 28 | 27 | 27 | 27 | 27 | 27 | 32 | 22 | — | — |
| Yield (m²/kg) | 36.6 | 36.6 | 36.6 | 36.6 | 36.6 | 36.6 | 36.6 | 31.4 | 43.9 | — | — |
| Specific density (g/cm³) | 0.91 | 0.91 | 0.91 | 0.91 | 0.91 | 0.91 | 0.91 | 0.91 | 0.91 | 0.91 | 0.92 |
| Haze (%) | 1.7 | 1.6 | 1.7 | 1.6 | 1.8 | 1.9 | 1.9 | 1.7 | 1.5 | 3.1 | 9.9 |
| Sheen (gloss), 45° (%) | 95.2 | 96.6 | 96.8 | 95.2 | 96.2 | 95.8 | 95.3 | 96.3 | 97.4 | 86.6 | 66.4 |
| Shrinkage, 120° C./5 min (%) | | | | | | | | | | | |
| In MD | 3.0 | 3.5 | 3.5 | 3.0 | 3.0 | 3.5 | 3.0 | 3.0 | 3.2 | 3.5 | 4.5 |
| In TD | 1.0 | 0.5 | 1.0 | 1.0 | 0.5 | 1.0 | 0.5 | 1.0 | 1.0 | 0.25 | 2.0 |
| Tensile strength at break (kg/mm²), | | | | | | | | | | | |
| in MD | 13.8 | 12.6 | 14.2 | 12.9 | 12.3 | 14.1 | 12.8 | 12.3 | 12.1 | 13.5 | 13.6 |
| In TD | 26.4 | 24.2 | 27.3 | 24.1 | 27.4 | 26.8 | 28.7 | 25.4 | 25.7 | 30.7 | 25.1 |
| Elongation break (%) | | | | | | | | | | | |
| In MD | 195 | 193 | 196 | 195 | 198 | 197 | 195 | 185 | 193 | 218 | 183 |
| In TD | 58 | 57 | 58 | 59 | 56 | 58 | 58 | 55 | 50 | 50 | 65.9 |
| Water vapor transmission (g/m² 24 h atm 20° C.) | 4.1 | 4.3 | 4.1 | 4.2 | 4.4 | 4.2 | 4.2 | 4.0 | 5.7 | ≧15 | — |

TABLE 2-continued

Physical-mechanical properties of the present invention (E1–E9), patented (A), and commercial (B) antifogging films.

| Properties | E1 | E2 | E3 | E4 | E5 | E6 | E7 | E8 | E9 | Patented Films A* | B* |
|---|---|---|---|---|---|---|---|---|---|---|---|
| Oxygen permeability (cc/m² 24 h atm 20° C.) | 1570 | 1595 | 1540 | 1615 | 1565 | 1605 | 1570 | 1450 | 1950 | ≧3000 | — |
| Friction coefficient, | | | | | | | | | | | |
| Film/Film | 0.23 | 0.28 | 0.25 | 0.23 | 0.25 | 0.27 | 0.25 | 0.25 | 0.22 | 0.23 | 0.22 |
| Film/Metal | 0.20 | 0.22 | 0.18 | 0.20 | 0.22 | 0.20 | 0.22 | 0.20 | 0.25 | 0.22 | 0.25 |
| Heat seal initiation temperature at g/10 mm (° C.) | 120 | 120 | 120 | 120 | 120 | 120 | 120 | 120 | 120 | 125 | 125 |
| Antifogging property** | E | E | E | E | E | E | E | E | E | D | C |
| Surface tension (after storage for 6 months) (nM/m) | 40/40 | 40/40 | 40/40 | 40/40 | 40/40 | 40/40 | 40/40 | 40/40 | 40/40 | 37/39 | 37/32 |

*A - U.S. Pat. No. 4,876,146
*B - Commercial film
**E (Excellent), D (Good), and C (Poor) in accordance with ICI "Cold-Fog" test method.

TABLE 3

Antifogging properties of the present invention (E1–E9), patented and commercial antifogging films.

Antifogging properties of films obtained by ICI "Cold-Fog" test method*

| Example No. | Antifogging side(s) of the examples of the present invention | Description | Performance | Rating | Comments |
|---|---|---|---|---|---|
| E1 | A | A transparent film displaying no visible water | Excellent | E | Completely Transparent |
| E2 | A | As in E1 | Excellent | E | As in E1 |
| E3 | A | As in E1 | Excellent | E | As in E1 |
| E4 | A, E | As in E1 | Excellent | E | As in E1 |
| E5 | A, E | As in E1 | Excellent | E | As in E1 |
| E6 | A, E | As in E1 | Excellent | E | As in E1 |
| E7 | A, E | As in E1 | Excellent | E | As in E1 |
| E8 | A, E | As in E1 | Excellent | E | As in E1 |
| E9 | A, E | As in E1 | Excellent | E | As in E1 |
| Patented | — | Randomly scattered transparent drops | Good | D | Discontinuous film of water |
| Commercial | — | A complete layer of large transparent drops | Poor | C | Poor Visibility, lens effect, dripping |

*As described in ICI publication 90-6E entitled "Antifog Evaluations Tests for Agricultural and Food-Packaging Film":

| Description | Performance | Rating | Comments |
|---|---|---|---|
| An opaque layer of small fog droplets | Very poor | A | Zero visibility |
| An opaque or transparent layer of small fog droplets | Poor | B | Zero visibility |
| A complete layer of large transparent droplets | Poor | C | Poor visibility |
| Randomly scattered large droplets | Good | D | Discontinous film of water |
| A transparent film with no visible water | Excellent | E | Completely transparent |

What is claimed is:

1. An antimicrobial and antifogging coextruded and oriented film having at least three layers comprising:

an outer layer comprising a polymer selected from the group consisting of polypropylene homopolymer, ethylene-propylene-n-butene terpolymers, ethylene-propylene copolymers, ethylene-n-butene copolymers and mixtures thereof;

a skin layer comprising at least one antimicrobial agent, at least one antifogging agent, and a polymer selected from the group consisting of polypropylene homopolymer, ethylene-propylene-n-butene terpolymers, ethylene-propylene copolymers, ethylene-n-butene copolymers and mixtures thereof and a core layer between the outer layer and the skin layer, comprising a polymer selected from the group consisting of polypropylene homopolymer, ethylene-propylene-n-butene terpolymers, ethylene-propylene copolymers, ethylene-n-butene copolymers and mixtures thereof.

2. The antimicrobial and antifogging film according to claim 1, wherein the at least one antifogging agent of the skin layer is a mixture of glycerol monostearate and diethanolamine.

3. The antimicrobial and antifogging film according to claim 2, wherein the at least one antifogging agent further comprises a special additive selected from the groups consisting of high fatty acid esters of polyvinyl alcohol or polyether polyol wherein the special additive enhances the antifogging properties of the film.

4. The antimicrobial and antifogging film according to claim 1, wherein the skin layer comprises a corona treated surface.

5. The antimicrobial and antifogging film according to claim 1, wherein the antimicrobial agent of the skin layer is an $Ag^+$-containing polymeric bioactive agent.

6. The antimicrobial and antifogging film according to claim 5, wherein the $Ag^+$-containing polymeric bioactive agent comprises at least 0.1 wt. % of the skin layer and has antibacterial activity against *Staphylococcus aureus, Eseherichia. coli* and *Salmonella enteritidis.*

7. The antimicrobial and antifogging film according to claim 1, wherein the core layer further comprises at least one antifogging agent.

8. The antimicrobial and antifogging film according to claim 7, wherein the at least one antifogging agent of the core layer is a mixture of glycerol monostearate and diethanolamine.

9. The antimicrobial and antifogging film according to claim 7, wherein the at least one antifogging agent further comprises a special additive selected from the groups consisting of high fatty acid esters of polyvinyl alcohol or polyether polyol wherein the special additive enhances the antifogging properties of the film.

10. The antimicrobial and antifogging film according to claim 1, wherein the core layer thickness is equal or greater than 10 microns thick.

11. The antimicrobial and antifogging film according to claim 1, wherein the outer layer is printable.

12. The antimicrobial and antifogging film according to claim 11, wherein the printable outer layer comprises a corona treated surface.

13. The antimicrobial and antifogging film according to claim 1, wherein the outer layer is heat sealable.

14. The antimicrobial and antifogging film according to claim 1, wherein the outer layer further comprises at least one antimicrobial agent.

15. The antimicrobial and antifogging film according to claim 14, wherein the at least one antimicrobial agent of the outer layer is an $Ag^+$-containing polymeric bioactive agent.

16. The antimicrobial and antifogging film according to claim 1, wherein the outer layer further comprises at least one antifogging agent.

17. The antimicrobial and antifogging film according to claim 16, wherein the outer layer comprises a corona treated surface wherein the corona treated surface is printable.

18. The antimicrobial and antifogging film according to claim 16, wherein the at least one antifogging agent of the outer layer is a mixture of glycerol monostearate and diethanolamine.

19. The antimicrobial and antifogging film according to claim 18, wherein the at least one antifogging agent further comprises a special additive selected from the groups consisting of high fatty acid esters of polyvinyl alcohol or polyether polyol wherein the special additive enhances the antifogging properties of the film.

20. The antimicrobial and antifogging film according to claim 1, wherein the outer layer thickness is equal or greater than 0.5 microns thick.

21. The antimicrobial and antifogging film according to claim 1, wherein the skin layer thickness is equal or greater than 0.5 microns thick.

22. The antimicrobial and antifogging film according to claim 1, further comprising an inner layer between the skin layer and the core layer wherein the inner layer is selected from the group consisting of ethylene-propylene-n-butene terpolymers, ethylene-propylene copolymers, and mixtures thereof.

23. The antimicrobial and antifogging film according to claim 22, wherein the inner layer thickness is greater than 0.5 microns.

24. The antimicrobial and antifogging film according to claim 22, wherein the inner layer further comprises at least one antifogging agent.

25. The antimicrobial and antifogging film according to claim 24, wherein the at least one antifogging agent of the inner layer is a mixture of glycerol monostearate and diethanolamine.

26. The antimicrobial and antifogging film according to claim 25, wherein the at least one antifogging agent further comprises a special additive selected from the groups consisting of high fatty acid esters of polyvinyl alcohol or polyether polyol wherein the special additive enhances the antifogging properties of the film.

27. The antimicrobial and antifogging film according to claim 1, further comprising a second inner layer between the outer layer and the core layer wherein the second inner layer is selected from the group consisting of ethylene-propylene-n-butene terpolymers, ethylene-propylene copolymers, and mixtures thereof.

28. The antimicrobial and antifogging film according to claim 27, wherein the second inner layer thickness is equal or greater than 0.5 microns thick.

29. The antimicrobial and antifogging film according to claim 27, wherein the second inner layer further comprises at least one antifogging agent.

30. The antimicrobial and antifogging film according to claim 29, wherein the at least one antifogging agent of the second inner layer is a mixture of glycerol monostearate and diethanolamine.

31. The antimicrobial and antifogging film according to claim 30, wherein the at least one antifogging agent further comprises a special additive selected from the groups consisting of high fatty acid esters of polyvinyl alcohol or polyether polyol wherein the special additive enhances the antifogging properties of the film.

32. The antimicrobial and antifogging film according to claim 1, wherein the comprising a skin layer and outer layer, are both heat sealable and wherein the skin layer is useful for food packaging and outer layer useful for printing.

33. The antimicrobial and antifogging film according to claim 1, wherein the antimicrobial and antifogging film is biaxially oriented.

34. An antimicrobial and antifogging coextruded and oriented film having at least three layers comprising:
   an outer layer comprising a polymer selected from the group consisting of polypropylene homopolymer, ethylene-propylene-n-butene terpolymers, ethylene-propylene copolymers, ethylene-n-butene copolymers and mixtures thereof;

a skin layer comprising an $Ag^+$-containing polymeric bioactive agent, a mixture of glycerol monostearate and diethanolamine, and a polymer selected from the group consisting of polypropylene homopolymer, ethylene-propylene-n-butene terpolymers, ethylene-propylene copolymers, ethylene-n-butene copolymers and mixtures thereof and a core layer between the outer layer and the skin layer, comprising a polymer selected from the group consisting of polypropylene homopolymer, ethylene-propylene-n-butene terpolymers, ethylene-propylene copolymers, ethylene-n-butene copolymers and mixtures thereof.

35. The antimicrobial and antifogging film according to claim 34, wherein the skin layer comprises a corona treated surface.

36. The antimicrobial and antifogging film according to claim 35, wherein the skin layer further comprises a special additive selected from the groups consisting of high fatty acid esters of polyvinyl alcohol or polyether polyol wherein the special additive enhances the antifogging properties of the film.

37. The antimicrobial and antifogging film according to claim 36, wherein the core layer further comprises a mixture of glycerol monostearate and diethanolamine.

38. The antimicrobial and antifogging film according to claim 37, wherein the core layer further comprises a special additive selected from the groups consisting of high fatty acid esters of polyvinyl alcohol or polyether polyol wherein the special additive enhances the antifogging properties of the film.

39. The antimicrobial and antifogging film according to claim 36, further comprising an inner layer between the skin layer and the core layer wherein the inner layer is selected from the group consisting of ethylene-propylene-n-butene terpolymers, ethylene-propylene copolymers, and mixtures thereof.

40. The antimicrobial and antifogging film according to claim 39, wherein the inner layer further comprises a mixture of glycerol monostearate and diethanolamine.

41. The antimicrobial and antifogging film according to claim 40, wherein the inner layer further comprises a special additive selected from the groups consisting of high fatty acid esters of polyvinyl alcohol or polyether polyol wherein the special additive enhances the antifogging properties of the film.

42. The antimicrobial and antifogging film according to claim 36, further comprising a second inner layer between the outer layer and the core layer wherein the second inner layer is selected from the group consisting of ethylene-propylene-n-butene terpolymers, ethylene-propylene copolymers, and mixtures thereof.

43. The antimicrobial and antifogging film according to claim 42, wherein the second inner layer further comprises a mixture of glycerol monostearate and diethanolamine.

44. The antimicrobial and antifogging film according to claim 43, wherein the second inner layer further comprises a special additive selected from the groups consisting of high fatty acid esters of polyvinyl alcohol or polyether polyol wherein the special additive enhances the antifogging properties of the film.

45. The antimicrobial and antifogging film according to claim 35, wherein the outer layer comprises a corona treated surface.

46. The antimicrobial and antifogging film according to claim 45, wherein the outer layer further comprises a mixture of glycerol monostearate and diethanolamine.

47. The antimicrobial and antifogging film according to claim 46, wherein the outer layer further comprises a special additive selected from the groups consisting of high fatty acid esters of polyvinyl alcohol or polyether polyol wherein the special additive enhances the antifogging properties of the film.

48. The antimicrobial and antifogging film according to claim 47, wherein the outer layer further comprises an $Ag^+$-containing polymeric bioactive agent.

49. The antimicrobial and antifogging film according to claim 45, wherein the outer layer further comprises an $Ag^+$-containing polymeric bioactive agent.

50. The antimicrobial and antifogging film according to claim 35, wherein the outer layer is printable and heat sealable.

* * * * *